United States Patent [19]

Lee

[11] 4,211,877

[45] Jul. 8, 1980

[54] METHOD OF PREPARATION OF ISOPROPYL 4,10-DIHYDRO-10-OXOTHIENO[3,2-c][1]BENZOXEPIN-8-ACETATE

[75] Inventor: Thomas B. K. Lee, Whitehouse Station, N.J.

[73] Assignee: American Hoechst Corporation, Bridgewater, N.J.

[21] Appl. No.: 11,943

[22] Filed: Feb. 13, 1979

[51] Int. Cl.$^2$ .......................................... C07D 495/02
[52] U.S. Cl. ........................................ 549/44; 549/71
[58] Field of Search ...................... 260/327 B; 549/44

[56] References Cited

U.S. PATENT DOCUMENTS 4,025,640   5/1977   McFadden et al. ......... 260/327 B X

OTHER PUBLICATIONS

Aultz et al., Chemical Abstracts, vol. 86, Abst. No. 133,345p (1977).
Degering, An Outline of Organic Chemistry, 6th ed. pp. 86 to 89, Barnes and Noble, Inc., NY (1951).

*Primary Examiner*—John D. Randolph
*Attorney, Agent, or Firm*—Curtis, Morris & Safford

[57] ABSTRACT

Isopropyl 4,10-dihydro-10-oxothieno[3,2-c][1]benzoxepin-8-acetate is synthesized from 4-(2-carboxy-3-thienylmethoxy)phenylacetic acid by a process comprising acid halide formation, ring closure catalyzed by aluminum trihalide and esterification with isopropyl alcohol. The three reaction steps are carried out successively in the same reactor without any isolation or purification of intermediate products and a surprisingly high overall yield is obtained. Additionally, a valuable chemical, aluminum isopropoxide is obtained as a by-product of this process and significant advantages in terms of environmental pollution and waste water costs are achieved.

7 Claims, No Drawings

METHOD OF PREPARATION OF ISOPROPYL 4,10-DIHYDRO-10-OXOTHIENO[3,2-C][1]BENZOXEPIN-8-ACETATE

This invention relates to a method of synthesizing the isopropyl 4,10-dihydro-10-oxothieno[3,2-c][1]-benzoxepin-8-acetate.

Compounds of the formula

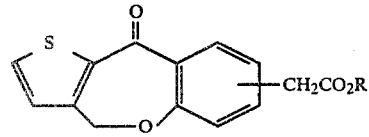

where R is hydrogen or loweralkyl group have been disclosed and claimed in the McFadden U.S. Pat. No. 4,025,640 filed Aug. 26, 1975 as having antiinflammatory and analgesic activities. The compounds are also disclosed and claimed in the Takawa et al. Japanese Patent Application No. 61607/1975, filed May 23, 1975 and published Nov. 26, 1976. While the disclosure in McFadden and Takawa are not limited to the particular compounds shown below, they describe two alternative routes of synthesis:

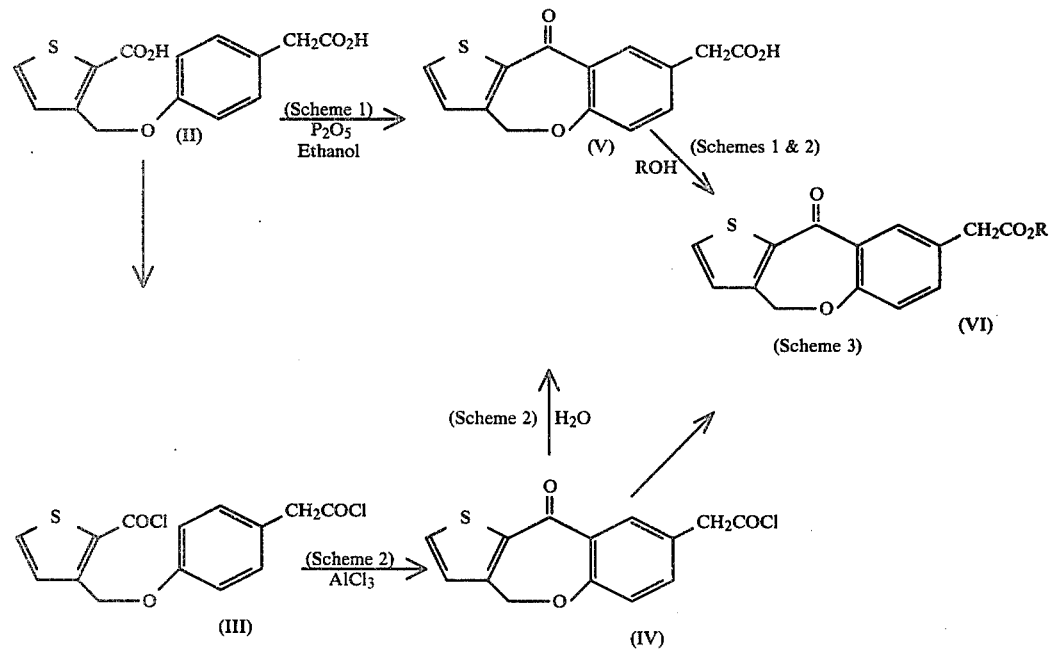

In both Scheme 1 and Scheme 2 of the above reaction sequences, the intermediate compound V is isolated and esterification is carried out subsequently in a separate step.

In my attempt to improve the overall yield of the compound VI, isopropyl 4,10-dihydro-10-oxothieno[3,2-c][1]-benzoxepin-8-acetate, I have found that various unexpected advantages can be obtained by carrying out the multiple reaction steps involved in the synthesis of said compound, in situ (Scheme 3), eliminating the formation and isolation of the intermediate compount V. Thus, according to the method of this invention, the starting compound II is first converted to the acyl halide by a suitable reagent such as $SOCl_2$ or $SOBr_2$, next ring closure is carried out by adding a Friedel-Crafts catalyst, specifically aluminum chloride or bromide to the reactor, and then, without forming the intermediate product V by hydrolysis, isopropyl alcohol is further added to the reactor. These operations can be carried out at temperatures of the order of about 0° to about 25° C., preferably within a range of about 5° to 15° C. in a suitable solvent, preferably a halogenated solvent, such as methylene or 1,2-dichloroethane. There is no need to add a catalyst such as sulfuric acid to effectuate the esterification. It should be noted that the esterification is carried out on the acyl halide, not on the free carboxylic acid V and also that aluminum chloride or bromide is converted to aluminum isopropoxide.

One advantage of the method of this invention is that the overall yield of the final component VI from the starting compound II is vastly improved, not only over the previously known method of Scheme 2, but also over the known method of Scheme 1. This is unexpected in view of the sequential combination in one reaction vessel of three reactions, each capable of multiple by-products and side reactions.

Another advantage of the method of this invention is its simplicity in comparison to the known Schemes 1 and 2, because it eliminates the formation and isolation of the intermediate compound V and all the successive reaction steps are carried out in situ.

Still another advantage of the method of this invention is that the aluminum catalyst is not wasted, but is recovered as aluminum isopropoxide, a valuable and saleable compound having various chemical applications, particularly for synthetic purposes, e.g. in Meerwein-Ponndorf-Verley reductions, by simple filtration followed by washing with a suitable solvent. This facile recovery of aluminum isopropoxide is highly advantageous from an economic and environmental standpoint as well in that it decreases the overall process costs for treatment of waste water by essentially eliminating the aluminum salts therefrom.

The invention, and its advantage over prior art processes, is further illustrated by the following example.

EXAMPLE

A mixture of 292.3 g of 4-(2-carboxy-3-thienylmethoxy)-phenylacetic acid, 500 ml of methylene chloride of 1,2-dichloroethane, 182.3 ml of thionyl chloride and 5 ml of N,N-dimethylformamide is heated with stirring to 28–30° C. over a period of 15 minutes and then kept at that temperature for 5½ hours. The reaction mixture is refluxed (pot temperature=40° C.) for an hour and then aged at room temperature for 16 hours.

An additional 500 ml of methylene chloride of 1,2-dichloroethane are added to the above crude acid chloride solution. This solution is cooled to 9°–10° C. in a cold water bath and 160 g of aluminum chloride are added portionwise such that the temperature of the reaction mixture is maintained between 10°–15° C. After addition, the mixture is stirred at 10°–12° C. for 2½ hours and then cooled to 0°–5° C. One liter of isopropyl alcohol is introduced slowly over a period of 1¼ hours, while maintaining the temperature <15° C. When all of the isopropyl alcohol is added, the mixture is allowed to warm to 20° C. over a period of 50 minutes. The resultant aluminum isopropoxide is filtered and washed with 500 ml of methylene chloride. The filtrate is successively extracted with cold (0°–5° C.) 1 N-HCl a mixed solution of 5% $NaHCO_3$ and 5% NaCl, and then with a solution of 5% NaCl. The organic layer is dried with 50 g of anhydrous magnesium sulfate and filtered. The $MgSO_4$ is washed with 120 ml methylene chloride. The combined filtrate is evaporated at reduced pressure and the residue is recrystallized from cyclohexane to afford 221 g (70% yield) of isopropyl 4,10-dihydro-10-oxothieno[3,2-c][1]-benzoxepin-8-acetate, mp 92°–94° C.

Analysis: Calculated for $C_{17}H_{16}SO_4$: 64.54%C; 5.10%H. Found: 64.42%C; 5.17%H.

In contrast, the method of Examples 1b and 3 of U.S. Pat. No. 4,025,640, which involves preparation and separation of 4,10-dihydro-10-exothieno[3,2-c][1]-benzoxepin-8-acetic acid crystals in a yield of 40% and subsequent esterification thereof to the isopropyl ester in a yield of 30% resulted in an overall yield of only 12% of the desired product.

I claim:

1. A method of synthesizing in situ isopropyl 4,10-dihydro-10-oxothieno[3,2-c][1]benzoxepin-8-acetate which comprises (a) halogenating 4-(2-carboxy-3-thienylmethoxy)-phenylacetic acid to form the diacid halide thereof; (b) treating said diacid halide with an aluminum halide to form a 4,10-dihydro-10-oxothieno[3,2-c][1]benzoxepin-8-acetylhalide; and (c) treating said acetylhalide with isopropyl alcohol to form the desired compound.

2. The method as defined in claim 1 wherein said aluminum halide is aluminum chloride.

3. The method as defined in claim 2 wherein said halogenating agent is thionyl chloride.

4. The method of claim 3 wherein step (a) is carried out in a halogenated solvent selected from the group consisting of methylene chloride and 1,2-dichloroethane.

5. The method of claim 4 wherein the cyclization is carried out at 10–15° C. and the treatment with isopropyl alcohol at 15° C.

6. The method as defined in claim 1 wherein said aluminum halide is aluminum bromide.

7. The method as defined in claim 4 wherein said halogenating agent is thionyl bromide.

* * * * *